(12) United States Patent
Hammond et al.

(10) Patent No.: US 6,214,187 B1
(45) Date of Patent: Apr. 10, 2001

(54) DENATURING GRADIENT AFFINITY ELECTROPHORESIS AND METHODS OF USE THEREOF

(75) Inventors: Philip W. Hammond, Ayer; T. Christian Boles, Lexington, both of MA (US)

(73) Assignee: Mosaic Technologies, Boston, MA (US)

( * ) Notice: Subject to any disclaimer, the term of this patent is extended or adjusted under 35 U.S.C. 154(b) by 0 days.

(21) Appl. No.: 09/336,228

(22) Filed: Jun. 18, 1999

Related U.S. Application Data

(60) Provisional application No. 60/089,788, filed on Jun. 18, 1998.

(51) Int. Cl.$^7$ ............... B01D 57/02; C12Q 1/68; C12P 19/34; C12M 1/34; G01N 33/00
(52) U.S. Cl. ............... 204/450; 435/6; 435/91.1; 435/287.2; 204/456; 204/466; 204/467; 436/94
(58) Field of Search ............... 435/6, 40, 91.1, 435/91.2, 283.1, 285.2, 975, 287.1, 287.2; 436/94, 501; 536/22.1, 23.1, 24.3, 24.33; 204/450, 456, 466, 467

(56) References Cited

U.S. PATENT DOCUMENTS

| | | | |
|---|---|---|---|
| 4,683,202 | 7/1987 | Mullis | 435/91 |
| 4,766,062 | 8/1988 | Diamond et al. | 435/6 |
| 4,766,064 | 8/1988 | Williams et al. | 435/6 |
| 4,829,098 | 5/1989 | Hoffman et al. | 522/5 |
| 4,830,726 | 5/1989 | Stamato et al. | 204/299 |
| 5,034,428 | 7/1991 | Hoffman et al. | 522/5 |
| 5,215,882 | 6/1993 | Bahl et al. | 435/6 |
| 5,237,016 | 8/1993 | Ghosh et al. | 525/329.4 |
| 5,310,650 | 5/1994 | McMahon et al. | 435/6 |
| 5,478,893 | 12/1995 | Ghose et al. | 525/329.4 |
| 5,482,836 | 1/1996 | Cantor et al. | 435/6 |
| 5,610,287 | 3/1997 | Nikiforov et al. | 526/24.3 |
| 5,641,658 | 6/1997 | Adams et al. | 435/91.2 |
| 5,679,524 | 10/1997 | Nikiforov et al. | 435/6 |
| 5,741,639 | 4/1998 | Ensing et al. | 435/6 |
| 5,830,711 | 11/1998 | Barany et al. | 435/91.1 |
| 5,932,711 | 8/1999 | Boles et al. | 536/22.1 |

FOREIGN PATENT DOCUMENTS

| | | |
|---|---|---|
| 0 671 626 A1 | 9/1995 | (EP) . |
| 0 703 296 A1 | 3/1996 | (EP) . |
| 3047097 | 2/1991 | (JP) . |
| WO 89/02930 | 4/1989 | (WO) . |
| WO 90/07582 | 7/1990 | (WO) . |
| WO 91/02815 | 3/1991 | (WO) . |
| WO 91/06850 | 5/1991 | (WO) . |
| WO 91/08307 | 6/1991 | (WO) . |
| WO 94/09156 | 4/1994 | (WO) . |
| WO 94/16108 | 7/1994 | (WO) . |
| WO 96/04404 | 2/1996 | (WO) . |
| WO 96/24687 | 8/1996 | (WO) . |
| WO 97/30346 | 8/1997 | (WO) . |
| WO 97/41256 | 11/1997 | (WO) . |
| WO 97/45554 | 12/1997 | (WO) . |
| WO 97/45721 | 12/1997 | (WO) . |
| WO 98/06872 | 2/1998 | (WO) . |
| WO 98/51823 | 11/1998 | (WO) . |

OTHER PUBLICATIONS

Borresen et al., Detection of base mutation in genomic DNA using denaturing gradient gel elctrophoresis (DGGE) followed by transfer and hybridization with gene–specific probes. Mutation Research 202, 77–83, 1988.*

Grompe, the rapid detection of unknown mutations in nucleic acids. Nature Genetics 5, 111–117, Oct. 1993.*

Baba et al., Specific base recognition of oligonucleotides by capillary affinity gel electrophoresis using polyacrylamide–poly(9–vinyladenine) conjugated gel. Anal. Biochem. 64, 1920–1925, 1992.*

Righetti et al., Non–isocratic capillary electrophoresis for detection of DNA point mutations. J. Chromatograph B, 697, 195–205, 1997.*

Wetmur, James G., "DNA Probes: Applications of the Principles of Nucleic Acid Hybridization," *Critical Reviews in Biochemistry and Molecular Biology*, 26(3/4) :227–259 (1991).

Tsurui, H., et al., "A rapid and efficient cloning method with a solid–phase DNA probe: application for cloning the 5' – flanking region of the gene encoding human fibronection," *Gene*, 88:233–239 (1990).

Timofeev, E.N., et al., "Regioselective immobilization of short oligonucleotides to acrylic copolymer gels," *Nucleic Acids Research*, 24 (16) :3142–3148 (1996).

Mergny, J–L, et al., "Fluorescence energy transfer as a probe for nucleic acid structures and sequences," *Nucleic Acids Research*, 22(6) :920–928 (1994).

Van Ness, J., et al., "A versatile solid support system for oligodeoxynucleotide probe–based hybridization assays," *Nucleic Acids Research*, 19(12) :3345–3350 (1991).

Nielsen, P.E., et al., "Sequence–Selective Recognition of DNA by Strand Displacement with a Thymine–Substituted Polyamide," *Science*, 254:1497–1500 (1991).

Jarrett, H.W., "Affinity chromatography with nucleic acid polymers," *Journal of Chromatography*, 618:315–339 (1993).

(List continued on next page.)

*Primary Examiner*—Bradley L. Sisson
*Assistant Examiner*—Frank Lu
(74) *Attorney, Agent, or Firm*—Hamilton, Brook, Smith & Reynolds, P.C.

(57) ABSTRACT

Methods are described for separation and analysis, and a kit for separation and analysis, of single nucleotide polymorphisms, or mutations, in target nucleic acid using denaturing gradient electrophoresis through supporting media containing one or more immobilized nucleic acid capture ligand. The method is especially useful for analyzing genetic haplotypes in samples with multiple linked polymorphic sites.

25 Claims, 5 Drawing Sheets

OTHER PUBLICATIONS

Barany, F., "Genetic disease detection and DNA amplification using cloned thermostable ligase," *Proc. Natl. Acad. Sci. USA*, 88:189–193 (1991).

Bing, D.H., et al., "Bridge Amplification: A Solid Phase PCR System for the Amplification and Detection of Allelic Differences in Single Copy Genes," http://www.promega.com/geneticidproc/ussymp7proc/0726.html, (Mar. 31, 1999).

Abrams, E.S., et al., "Bridge Amplification for DNA–based Diagnostics," *Diagnostic Gene Detection & Quantification Technologies for Infectious Agents & Human Genetic Diseases*, S.A. Minden et al., eds. (MA: International Business Communications, Inc.), pp. 171–189 (1997).

"A New Method for the Preparation of DNA–Cellulose," Analytical Biochemistry, 89:616–619 (1978).

Inami, Y., et al., "Affinity gel electrophoresis of nucleic acids. The interaction between water soluble polymers having malachite green and double–stranded DNAs," *Nucleic Acids Symp. Ser.*, 29:77–78 (1993).

Baba, Y., et al., "Specific Base Recognition of Oligodeoxynucleotides by Capillary Affinity Gel Electrophoresis Using Polyacrylamide–Poly(9–vinyladenine) Conjugated Gel," *Anal. Chem.*, 64:1920–1924 (1992).

Creighton, T.E., "Electrophoretic Analysis of the Unfolding of Proteins by Urea," *J. Mol. Biol.*, 129:253–264 (1979).

Fischer, S.G. and Lerman, L.S., "Length–Independent Separation of DNA Restriction Fragments in Two–Dimensional Gel Electrophoresis," *Cell*, 16:191–200 (1979).

Thatcher, D.R. and Hodson, B., "Denaturation of proteins and nucleic acids by thermal–gradient electrophoresis," *Biochem. J.*, 197:105–109 (1981).

Rosenbaum, V. and Riesner, D., "Temperature–gradient gel electrophoresis. Thermodynamic analysis of nucleic acids and proteins in purified form and in cellular extracts," *Biophys. Chem.*, 26:235–246 (1987).

Gelfi, C., et al., "Temperature–Programmed Capillary Electrophoresis for Detection of DNA Point Mutations," *BioTechniques*, 21(5):926–932 (1996).

Kennedy, M., et al., "Mutation Typing Using Electrophoresis and Gel–Immobilized Acrydite™ Probes," *BioTechniques*, 25(3):516–521 (1998).

Baba, Y., et al., "Base–specific separation of oligodeoxynucleotides by capillary affinity gel electrophoresis," *Electrophoresis*, 19:433–436 (1998).

Igloi, G.L., "Variability in the stability of DNA–peptide nucleic acid (PNA) single–base mismatched duplexes: Real–time hybridization during affinity electrophoresis in PNA–containing gels," *Proc. Natl. Acad. Sci. USA*, 95:8562–8567 (1998).

Ozaki, Y., et al., "Affinity capillary electrophoresis using DNA conjugates," *Nucleic Acids Symposium Series No. 37*:235–236 (1997).

Rehman, F.N., et al., "Immobilization of acrylamide–modified oligonucleotides by co–polymerization," *Nucleic Acids Research*, 27(2):649–655 (1999).

Penner, G.A., et al., "Increased detection of polymorphism among randomly amplified wheat DNA fragments using a modified temperature sweep gel electrophoresis (TSGE) technique," *Nucleic Acids Research*, 22(9):1780–1781 (1994).

* cited by examiner

SEQUENCE LISTING

```
<160> NUMBER OF SEQ ID NOS:  11

<210> SEQ ID NO 1
<211> LENGTH: 54
<212> TYPE: DNA
<213> ORGANISM: Artificial Sequence
<220> FEATURE:
<223> OTHER INFORMATION: Synthetic construct

<400> SEQUENCE: 1
tcgtcccttt gctgcgtgac gtcgtggtcc ggcgcatggc ttctattggg tgcc         54

<210> SEQ ID NO 2
<211> LENGTH: 60
<212> TYPE: DNA
<213> ORGANISM: Artificial Sequence
<220> FEATURE:
<223> OTHER INFORMATION: Synthetic construct

<400> SEQUENCE: 2
tcgtcccttt cctgcgtgac gtcgtggtcc ggcgcatggc ttctattggg tgccagcaag   60

<210> SEQ ID NO 3
<211> LENGTH: 36
<212> TYPE: DNA
<213> ORGANISM: Artificial Sequence
<220> FEATURE:
<223> OTHER INFORMATION: Synthetic construct

<400> SEQUENCE: 3
agggaaacga cgcactttt taccgaaggt aaccca                               36

<210> SEQ ID NO 4
<211> LENGTH: 16
<212> TYPE: DNA
<213> ORGANISM: Artificial Sequence
<220> FEATURE:
<223> OTHER INFORMATION: Synthetic construct

<400> SEQUENCE: 4
agggaaacga cgcact                                                    16

<210> SEQ ID NO 5
<211> LENGTH: 16
<212> TYPE: DNA
<213> ORGANISM: Artificial Sequence
<220> FEATURE:
<223> OTHER INFORMATION: Synthetic construct

<400> SEQUENCE: 5
taccgaaggt aaccca                                                    16

<210> SEQ ID NO 6
<211> LENGTH: 13
```

-continued

```
<212> TYPE: DNA
<213> ORGANISM: Artificial Sequence
<220> FEATURE:
<223> OTHER INFORMATION: Synthetic construct

<400> SEQUENCE: 6
gcagggaaag gac                                                          13

<210> SEQ ID NO 7
<211> LENGTH: 13
<212> TYPE: DNA
<213> ORGANISM: Artificial Sequence
<220> FEATURE:
<223> OTHER INFORMATION: Synthetic construct

<400> SEQUENCE: 7
actgcagcac cag                                                          13

<210> SEQ ID NO 8
<211> LENGTH: 13
<212> TYPE: DNA
<213> ORGANISM: Artificial Sequence
<220> FEATURE:
<223> OTHER INFORMATION: Synthetic construct

<400> SEQUENCE: 8
cgcgtaccga aga                                                          13

<210> SEQ ID NO 9
<211> LENGTH: 13
<212> TYPE: DNA
<213> ORGANISM: Artificial Sequence
<220> FEATURE:
<223> OTHER INFORMATION: Synthetic construct

<400> SEQUENCE: 9
acccacggtc gtt                                                          13

<210> SEQ ID NO 10
<211> LENGTH: 21
<212> TYPE: DNA
<213> ORGANISM: Artificial Sequence
<220> FEATURE:
<223> OTHER INFORMATION: Synthetic construct

<400> SEQUENCE: 10
ttggttggtt tatcgttttt g                                                 21

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
caaaaacgat aaaccaacca                                                   20
```

DENATURING GRADIENT AFFINITY ELECTROPHORESIS AND METHODS OF USE THEREOF

RELATED APPLICATION

This application claims the benefit of U.S. Provisional Application No. 60/089,788, filed on Jun. 18, 1998, entitled "Denaturing Gradient Affinity Electrophoresis (DGAE)," the entire teachings of which are incorporated herein by reference.

BACKGROUND OF THE INVENTION

Zonal electrophoresis, and particularly gel electrophoresis is one of the best known methods for separation, purification and characterization of charged molecules, particularly macromolecules such as proteins or nucleic acids (Freifelder, *Physical Biochemistry*, 2nd ed., (1982) pp. 276–310, Freeman, San Franciso). Electrophoresis can be used to separate molecules based on their size, charge, conformation, and many combinations of these properties.

In most electrophoresis applications, charged molecules migrate through a supporting medium under the influence of an electric field. The supporting medium acts to suppress convection and diffusion, and can be sieving or nonsieving. In affinity electrophoresis, the support medium is also modified with chemical groups (hereinafter "capture ligands") that interact specifically or nonspecifically with one or more desired targets and, thus, help to accomplish the separation of target and non-target sample components during purification by influencing the mobility of the target.

Affinity electrophoresis has been used to enhance the separtion of nucleic acids. For example, Inami, et al. demonstrated that A:T-rich sequences of nucleic acids have an affinity for malechite green copolymerized with acrylamide and immobilized within an agarose gel (Inami, et al., *Nucleic Acids Symp. Ser.* (19 ) 29:77–8). In addition, vinyl-adenine modified polyacrylmide media has been used to resolve nucleic acids in capillary electrophoresis (Baba et al., *Analytical Chemisty* (1992), 64:1920–1924).

Electrophoresis techniques have been used by biochemist to study melting transitions. Electrophoretic mobility is a very sensitive indicator of protein and nucleic acid conformation and, therefore, electrophoresis is a very useful or studying melting induced by chemical or physical denaturants. Gels containing gradients of urea have been used to study the binding of proteins (Creighton, *J Mol. Biol.* (1979) 129:253–264) and melting behavior of nucleic acids (Fischer, et al., Cell (1979)16:191–200).

Temperature gradients have also been used to study these properties with similar results (Thatcher, et al., *Biochem. J* (1981), 197:105–109), and many methods of producing temperature gradients have been developed (Henco, et al., *Methods Mol. Biol.* (1994) 31:211–28 and Rosenbaum, et al., *Biophys. Chem.* (1987) 26:235–246).

While many advances have been made in the resolving power of electrophoresis, nucleic acids that contain only slight structural differences, for example, one or more point mutation in a long nucleic acid sequence, still cannot be successfully separated.

Analytical techniques that improve resolution of biological molecules are needed to provide researchers with the opportunity to further probe and understand biological systems.

SUMMARY OF THE INVENTION

The present invention relates to a method for analyzing, separating or purifying a target nucleic acid. The method uses an electrophoresis medium that has one or more nucleic acid capture ligands (also referred to herein as "capture robes") immobilized throughout the medium. In addition, a spatial gradient of a nucleic acid denaturant exists within the electrophoresis medium so that a sample migrates from a region of high denaturant activity to a region of lower denaturant activity during electrophoresis. One or more target nucleic acids are electrophoresed through the medium under conditions that allow binding of the target to the immobilized capture ligand at a position within the medium that is related to the sequence complementarity of the target and the capture ligand. For example, if a sample contains a target nucleic acid which has a sequence that has complete complementarity to the capture ligand (i.e., fully complementary to the nucleotide sequence of the capture ligand) and a target nucleic acid sequence that has incomplete complementarity with the capture ligand (e.g., a single nucleotide mismatch), the target nucleic acid that has complete complementarity to the capture ligand will bind to the capture ligand at a position in the medium where denaturant activity is relatively high (e.g., high temperature or high concentration of chemical denaturant). The target nucleic acid that has incomplete complementarity with the capture ligand will migrate further into the medium and bind a capture ligand at a position of lower denaturing activity (e.g., lower temperature or lower concentration of chemical denaturant).

To analyze a target nucleic acid sequence, the location of he target within the medium is determined and compared to the location within the medium of a standard nucleic acid having a predetermined sequence, or binding affinity. The location of the target within the medium is dependent on the nucleotide sequence or structure of the target nucleic acid, and its complementarity to and binding affinity for the immobilized capture ligand. The target nucleic acid will stop migrating at a position within the medium where the denaturing activity is low enough to allow a table binding complex to form. Thus, the target nucleic acid will bind to the immobilized capture ligand at a position within the medium that is relative to the binding affinity between the target and the capture ligand.

Alternatively, a property related to the location of the target within the medium, such as the time it takes for a target to pass a position in the medium that is scanned by a detector can be determined. For example, once nucleic acid sequences in a sample have been separated based on their affinity to a capture ligand using the denaturing gradient affinity electrophoresis method described above, the denaturant (e.g., temperature or chemical denaturant) can be increased to a point where the capture ligand and the target having the highest degree of complementarity to the capture ligand are denatured. For example, the temperature can be raised above the Tm for the capture ligand/target complex. Once the capture ligand/target complex has been denatured, an electric field can be applied and the target nucleic acids in the sample can be electrophoresed under standard conditions for denaturing electrophoresis. If a detector is detecting a position in the medium which is at the opposite end of the medium from the region where the sample was introduced and is at a distance, measured along the path which the target nucleic acids have migrated, further away from where the sample is introduced than any one of the target nucleic acids have migrated during the denaturing gradient affinity electrophoresis step, the target nucleic acids will pass this position at different times because they have already been separated based on their complementarity to the capture ligand in the denaturing gradient affinity electrophoresis step. This embodiment is particularly useful in capillary denaturing gradient affinity electrophoresis where the detector is located at one end of the capillary and the time at which a target nucleic acid passes the position where the detector located is the property which is determined. In addition, this embodiment can be applied to gel electrophoresis systems where a detector scans a line across the gel at the opposite end of the gel from the sample wells to determine the time at which target nucleic acid passes this line. The present invention also encompasses a kit for analyzing the nucleic acid sequence of a test sample for the presence of a degenerate site, or mutation. The kit has an electrophoretic medium that has at least one capture ligand that as a sequence which is complementary to a region of the nucleic acid sequence of the target which contains the degenerate site, or mutation. The kit also has a means for creating a gradient of a nucleic acid denaturant in the electrophoretic medium.

The method of the present invention is operationally simple, and relies on well- understood principles of DNA hybridization. In addition, the use of a gradient of denaturing conditions minimizes the amount of assay optimization required to obtain high quality results. This is particularly important, since traditional hybridization-based methods for detection of single nucleotide polymorphisms are frequently time-consuming to optimize. The method of the invention is particularly useful for mutation typing and can be easily adaptable to capillary electrophoresis platforms for high throughput, automated typing on large numbers of samples. The potential for distinguishing targets based on multiple genetically linked polymorphisms is particularly useful, since many important biological phenotypes are dependent on haplotypes composed of a defined set of markers.

DETAILED DESCRIPTION OF THE INVENTION

Figure 1:
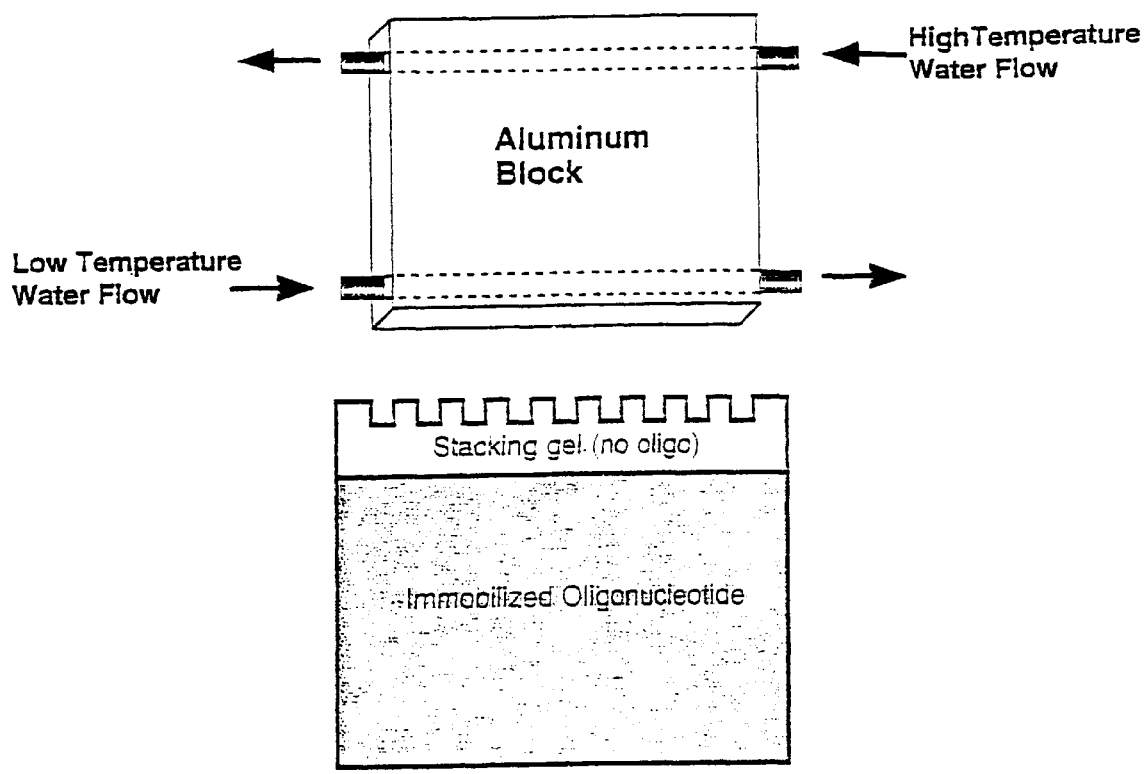
FIG. 1 is a drawing depicting a device for performing thermal gradient affinity electrophoresis.

The invention disclosed herein is directed to a method for nucleic acid separation and sequence analysis and a kit for detecting a mutation in a target nucleic acid by denaturing gradient affinity electrophoresis. The method involves contacting a test sample with an electrophoretic medium comprising the following elements: 1) at least one nucleic acid capture ligand, and 2) a spatial gradient of a nucleic acid denaturant. The spatial gradient of nucleic acid denaturant is most active in the area where the sample is first contacted with the electrophoretic medium. An electric field is applied in a direction parallel to the gradient of the nucleic acid denaturant so that the sample migrates from an area of higher denaturing activity to an area of lower denaturing activity. As the sample migrates, it will bind (i.e., hybridize) to a complementary capture ligand under suitable conditions. The method allows a nucleic acid component of a test sample containing a sequence which is complementary to the capture ligand to be distinguished from other components of the sample.

The combination of these features results in a novel invention that has broad utility for separation, analysis, purification and detection of nucleic acids having only minor variations in sequence based on the location of the nucleic acid in the medium or its mobility within the medium in comparison to a standard nucleic acid having a known sequence.

In a preferred embodiment, a test sample is introduced into the electrophoretic medium having at least one immobilized capture ligand in an area of the medium where the denaturing gradient is most active, typically at the top of the medium. In this area of the medium, nucleic acid components of the test sample do not bind (i.e., hybridize) to the capture ligand because of the strength of the denaturing activity. When an electric field is applied, charged components of the test sample move in direction parallel to the denaturing gradient towards an area of the medium where the denaturing gradient is less active. As the denaturing activity decreases, nucleic acid components of the test sample that have a portion of, or region of, their nucleotide sequence complementary to the nucleotide sequence of the capture ligand bind to the capture ligand. This causes their rate of migration through the medium to be retarded. Eventually, as the target nucleic acid continues to migrate through the medium, it will reach a position in the medium where the denaturing activity will be low enough to allow a stable binding complex to form between the target and the capture ligand. At this position, the progress of the target through the medium will stop. Since a nucleic acid with one or more mismatched nucleotides binds to the capture ligand less strongly than a nucleic acid that has a fully complementary sequence, their mobility is less retarded than a nucleic acid that has a fully complementary sequence. For example, the nucleic acids in the test sample can have significant nucleotide mismatch with the ligand and will migrate rapidly through the medium, or the mismatch can be a single base pair mismatch and they will migrate more slowly through the medium. Once denaturing activity is low enough nucleic acid targets which have mismatch will also reach a position in the medium where they will form a stable binding complex with the capture ligand. At this position, they will also stop migrating through the medium. Therefore, this technique can be used to identify nucleic acids that have sequences complementary to a capture ligand. In addition, nucleic acids with similar nucleotide sequences that differ by only one base, or only a few bases, can be distinguish from each other on the basis of the position where they stop migrating through the medium.

Figure 2:
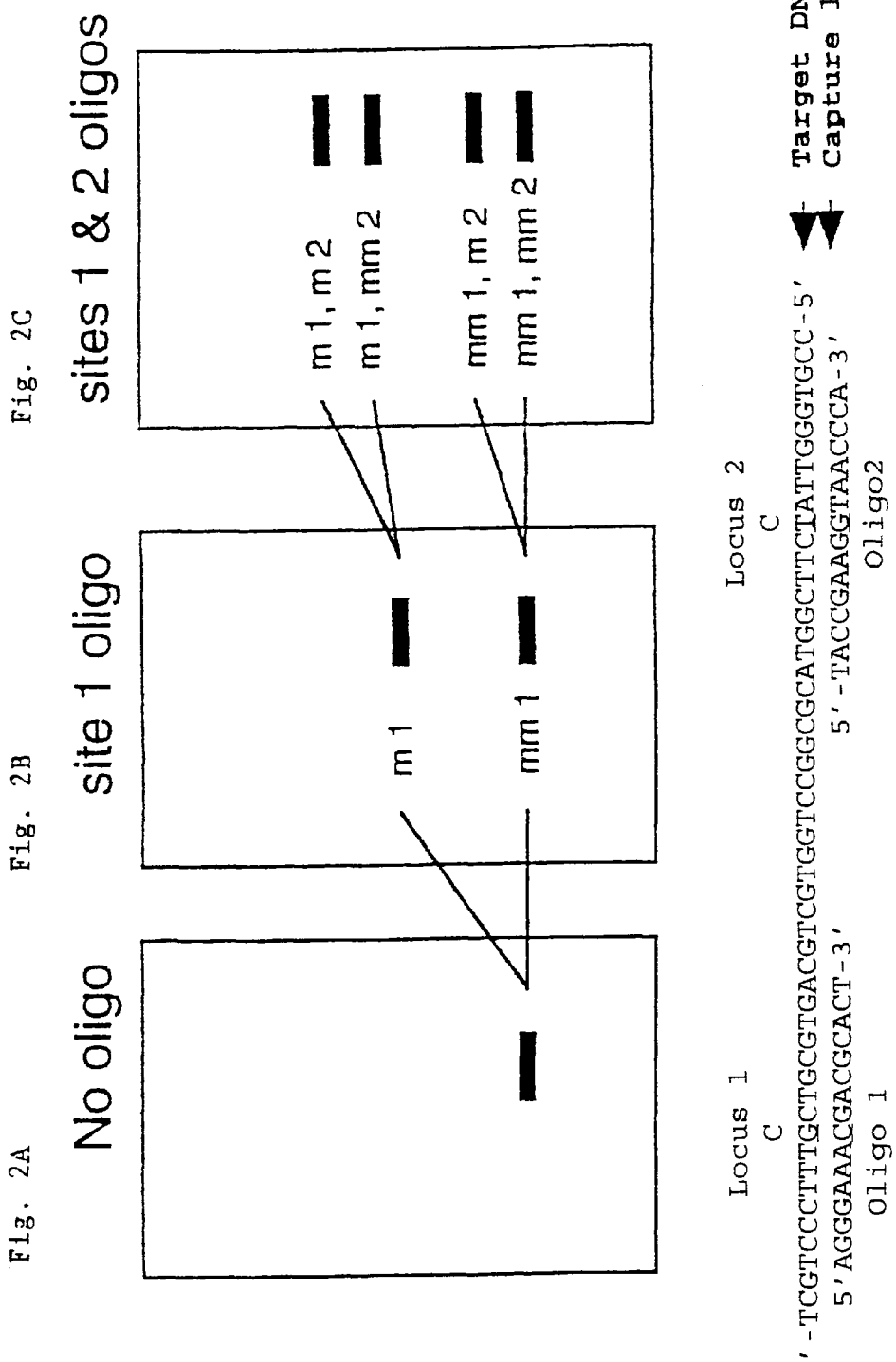
FIGS. 2A–2C are graphics illustrating the principle of denaturant gradient affinity electrophoresis of a target nucleic acid (SEQ ID NO:1) that has two biallelic markers labeled locus 1 and locus 2.

The basic principle of the method is illustrated by the example in FIG. 2. In FIGS. 2A–2C, the test sample is introduced at the top of a slab gel which has a temperature gradient imposed on it by an apparatus such as the one illustrate in FIG. 1. FIG. 1 depicts an apparatus for imposing a thermal gradient on a slab gel. The gel is prepared with an oligonucleotide (e.g., the oligonucleotide labeled capture ligand in FIG. 2) co-polymerized throughout the body of the gel. After assembly on suitable gel rig, an aluminum block is clamped to the glass plates such that the top port, or channel, for water flow is near the sample wells. By passing hot water through the top port of the plate and cold water through a port at bottom of the plate a temperature gradient is formed within the plate and also within the gel to which it is clamped.

FIGS. 2A–2C represent idealized gel images. Shown below FIGS. 2A–2C is the sequence of a target nucleic acid (SEQ ID NO: 1), which exhibits biallelic sequence polymorphisms at two closely linked loci (labeled locus 1 and locus 2) which are degenerate sites in the nucleic acid sequence of the target. A degenerate site is a site in a nucleic acid sequence wherein a base can vary. Loci 1 and 2 each have one degenerate site that is biallelic since it can have either a cytosine or a guanin 220 base. A degenerate site can also be a site which can have any one of the four bases (i.e, thymine, cytosine, guanine or adenine for DNA or uracil, cytosine, guanine, or adenine for RNA). The target shown in FIG. 2 can contain as many as four separate sequences because it has two biallelic sites. Also shown in FIG. 2 are the sequence of two ligonucleotide capture ligands, labeled Oligo 1 (SEQ ID NO: 4) and Oligo 2 (SEQ ID NO: 5), designed to type the two polymorphisms by binding to the portion of the target strand which spans locus 1 or locus 2, respectively. A capture ligand is designed to type a polymorphism, or degenerate site, if it is complementary to a region of the nucleic acid sequence surrounding the site and is complementary to one of the degenerate options at the degenerate site. For example, Oligo 1 (SEQ ID NO: 4) is complementary to the nucleic acid sequence surrounding locus 1 and is complement to locus 1 when locus 1 is a guanine. As used herein, a capture ligand is complementary to a region of the nucleic acid sequence of a target containing a degenerate site if least one of the bases which can be located at the degenerate site is complementary to the corresponding base on the capture ligand.

The three idealized gel images show the results expected after electrophoresis has been carried out in the device shown in FIG. 1 from gels containing no capture ligand (FIG. 2A), capture ligand Oligo 1 (SEQ ID NO: 4) only (FIG. 2B), and capture ligands Oligo 1 (SEQ ID NO: 4)and Oligo 2 (SEQ ID NO: 5) together (FIG. 2C). For all cases illustrated in FIG. 2, the samples are electrophoresed vertically through the gel from top to bottom. As the sample migrates through the gel, the target DNA passes into progressively cooler, less denaturing, regions of the gel.

In the gel without a capture ligand (FIG. 2A), all targets migrate at approximately similar rates because they are all the same length and, therefore, have similar molecular weights. The relatively small mobility shifts caused by single-strand conformational polymorphisms can be ignored.

In the gel containing capture ligand Oligo 1 (SEQ ID NO: 4) alone (FIG. 2B), a test sample containing both types of locus 1 alleles will show two bands. As the samples migrate through the gel, at some point the temperature becomes low enough so that the target with a sequence complementary to Oligo 1 (SEQ I NO: 4) binds stably to the Oligo 1 (SEQ ID NO: 4) capture ligands and, thereby becomes immobilized within the gel at that particular position. The position within the gel at which binding occurs depends on the stability of the binding complexes formed between capture ligand and target. In the example of FIG. 2, the binding reaction is base complementary base pairing. Thus, targets that show complete complementarity with the capture ligand will form stable binding complexes with the ligand at relatively high temperatures and, therefore, will stop moving relatively early. Targets that have mispairs with the capture ligand will form less stable binding complexes with the ligand, and will migrate further into the gel before becoming immobilized. In the example show in FIG. 2B, the "ml" allele stopped moving first and, therefore, would be complement to the capture ligand, and have a guanine at locus one. The "mml" allele stopped lower in the gel, demonstrating its lower affinity for the capture ligand and, therefore, would represent the allele having a cytosine at locus 1.

The method of the present invention can be extended to analyze linkage between two polymorphic sites. This is shown in FIG. 2C, where the gel contains both Oligo 1 (SEQ ID NO: 4) and Oligo 2 (SEQ ID NO: 5) capture ligands. In this gel the final position of the target depends on its affinity for two different capture ligands. For a target with two biallelic markers, four possible haplotypes are expected, and these will have distinguishable affinities for the capture ligands as illustrated in FIG. 2C.

In principle, haplotypes involving additional loci could be resolved as illustrated in FIGS. 3A–3D. For example, in FIG. 3, a target with four bialleic markers (i.e., Loci 1–4), is expected to have sixteen possible haplotypes that will have distinguishable mobilities when electrophoresed on a gel which has four allele specific nucleic acids capture ligands, Oligo 1 (SEQ ID NO: 6), Oligo 2 (SEQ ID NO: 7), Oligo 3 (SEQ ID NO: 8), and Oligo 4 (SEQ ID NO: 9), which are complementary to a sequence of the target which spans the each of the biallelic regions of the target.

Discussions of the key components of the invention and nonlimiting extensions are listed below:

TEST SAMPLE

The test sample can be any sample containing nucleic acids. The length of a target nucleic acid which can be analyzed conveniently by the method of the present invention is dependent on the pore size of the type of media used The target nucleic acid can be from five to several thousand nucleotides in length can be analyzed. For example, a target that is from 30 to 2000 nucleotides in length C be analyzed using a polyacrylamide medium. In one embodiment of the present invention, the entire nucleotide sequence of the target is complementary to the capture ligand. In another embodiment of the present invention, only a portion of the target nucleotide sequence is complementary to the capture ligand. For example, the target may be a sequence with a single polymorphic site comprising one, or more, nucleotides that are mismatched with the capture ligand.

Specifically encompassed by the present invention are samples from biological sources containing cells, obtained using known techniques, from body tissue (e.g., skin, hair, internal organs), or body fluids (e.g., blood, plasma, urine, semen, sweat). Other sources of samples suitable for analysis by the methods of the present invention are microbiological samples, such as viruses, yeasts and bacteria: plasmids, isolated nucleic acids and agricultural sources, such as recombinant plants. A target nucleic acid is any nucleic acid of interest that can form a binding complex with a capture ligand.

The test sample is treated in such a manner, known to those of skill in the art, so as to render the target nucleic acid contained in the test sample available for binding. For example, a cell lysate can be prepared, and the crude cell lysate (e.g., containing the target nucleic acid as well as other cellular components) can be analyzed. Alternatively, the target nucleic acid can be partially isolated (rendering the target substantially free from other cellular components)

prior to analysis. Partial isolation can be accomplished using known laboratory techniques. For example, DNA or RNA an be isolated from a variety of biological samples using TRI reagent (see Sigma catalogue, p. 1545, catalogue numbers T9424, T3809, and T3934, see also Chomczyski, et al., Biochem. (1987), 162:156; Chomczynski, Biotechniques (1993), 15:532) in conjuct with Southern blotting (DNA) or Northern blotting (RNA) procedure. Other sample preparation techniques can be found in Murray, et al., "Manual Clinical Microbiology, 6$^{th}$ edition", (1995), ASM Press, Washington, D.C.

For many applications of the invention, the preferred target will be single stranded nucleic acid. Asymmetric PCR products and naturally occurring single stranded nucleic acids such as RNA can be used directly, provided that they are detectable directly or can be detectably labeled.

Double-stranded nucleic acids can be rendered single-stranded by thermal or chemical denaturation prior to loading. For analysis of double-stranded DNA targets produced by the polymerase chain reaction (PCR), single stranded material can be obtained by thermal denaturation in formamide or by alkaline denaturing in a basic solution. For instance, most PCR products can be denatured in the presence of 75% formamide by incubation at temperatures greater than 60° C. for minutes. Alternatively, double-stranded PCR products generated using one biotinylated primer can be bound to streptavidin-coated magnetic particles, and the on-biotinylated strand can be released from the bead with mild base (0.1N NaOH), neutralized, and recovered in concentrated form by ethanol precipitation or ultrafiltration for analysis using the method of the invention.

Alternatively, double-stranded nucleic acids samples can be rendered single-stranded after or coincident with contact with the electrophoretic medium. In this technique, the denaturant activity in the portion of the electrophoretic medium where the sample is first contacted with the medium is high enough to denature a double-stranded nucleic acid and render it single stranded when it is contacted with the medium. In some cases, the double-stranded nucleic acid may not denature immediately when contacted with the electrophoretic medium, but may denature as it migrated through the portion of the medium where the denaturing activity is high. For example, in thermal gradient affinity electrophoresis on a slab gel, the temperature of the sample wells should be above the Tm of the double-stranded nucleic acid sample. If the temperature of the sample wells is significantly above the Tm of the double-stranded nucleic acid sample (e.g., 5° C. or more above the Tm), the double-stranded nucleic acid sample will denature when it is contacted with the electrophoretic medium.

CAPTURE LIGANDS THAT BIND TO A TARGET NUCLEIC ACID

Figure 4:
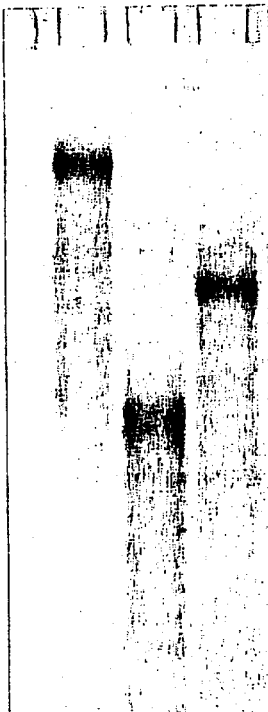
FIG. 4 is a photograph showing the results of an experiment using a model target and a capture ligand (SEQ ID NO:3) that has two capture sequences complementary to locus 1 and locus 2 of the target nucleic acid (SEQ ID NO:1).

A capture ligand is any nucleic acid or modified nucleic acid that can form a specific binding complex with a target nucleic acid and can be immobilized within a suitable electrophoretic medium. When a capture ligand forms a stable specific binding complex with a target, the mobility of the target, or the speed at which the target migrates through the medium, is lowered. The capture ligand can contain two or more distinct sequences, called capture sequences, that are complementary to two or more separate nucleic acid sequence regions within the target nucleic acid. When a capture ligand contains more than one capture sequence, the capture sequences can be separated by a nucleic acid sequence that is not complementary to a nucleic acid sequence on the target. FIG. 4 is an example of a capture ligand which has two capture sequences which are complementary to Locus 1 and locus 2 on the target nucleic acid (SEQ ID NO: 1) separated by a sequence of 4 thymidine nucleic acids which is non complementary to the target nucleic acid.

The nucleic acids of the present invention include deoxyribonucleic acid (hereinafter, "DNA"), ribonucleic acid (hereinafter, "RNA"), modified nucleic acids, and nucleic acid analogs such as peptide nucleic acid (hereinafter, "PNA") and morpholino nucleic acids. Both single stranded and double stranded nucleic acids capture ligands and targets are embraced by this invention. Higher ordered structures of nucleic acids, for example, RNA that has folded upon its linear strand forming a secondary loop structure, are also within the scope of the present invention. Nucleic acid sequences as used herein denote a nucleotide sequence from about 5 to about 50,000 nucleotides in length. There is no absolute length requirement for participating target nucleic acid sequence(s), however, as discussed above, a preferred range is from about 30 to about 2000 when the electrophoretic medium is a polacrylamide gel. Preferably, the capture ligand is from about 5 to about 1000 in nucleotide length. Most preferably, the capture ligand is from about 5 to about 100 in nucleotide length. In an even more preferred embodiment, the capture ligand is from abou5 to about 20 in nucleotide length. One of ordinary skill in the art will be able to determine the appropriate length of nucleotide sequence to employ for the nuleiu acids of the present invention. It should also be understood that the nucleic acid sequences of the present invention can be embedded within longer strands of nucleic acids or associated with other molecules, such as a peptide nucleic acid (PNA).

Base-pairing is generally understood to occur in an antiparallel manner, however, there are occasions in which base-pairing can occur in a parallel fashion and this arrangement is also within the scope of the present invention. Base-pairing itself is understood to essentially follow a complementary pattern wherein purine pairs with a pyrimidine via hydrogen bonds. More particularly, it is understood that complementary base-pairing of individual base pairs generally follows Chargaff's Rule wherein an adenine pairs with a thymine (or uracil) and guanine pairs with cytosine However, there are modified bases which account for unconventional base-pairing. A modified nucleic acid is understood to mean herein a DNA or RNA nucleic acid molecule that contains chemically modified nucleotides. The term "nucleic acid alogue" is understood herein to denote non-nucleic acid molecules such as PN (see Egholm, et al., *J Am. Chem. Soc.* (1992), 114:1895) and morpholino antisense ligomers (see Summerton and Weller, *Antisense and Nucleic Acid Drug Dev.* (1997), 7:187) that can engage in base-pairing interactions with conventional nucleic acids. These modified bases and nucleic acid analogues are considered to be within the cope of the instant invention. For example, nucleotides containing deazaguaine and uracil bases can be used in place of guanine and thymine, respectively, to decrease the thermal stability of hybridized probes. Similarly, 5-methylcytosine can be substitute for cytosine in hybrids if increased thermal stability is desired. Modification to the sugar moiety can also occur and is embraced by the present invention. For example, modification to the ribose sugar moiety through the addition of 2'-O-methyl groups which can be used to reduce the nuclease susceptibility of RNA molecules. Modifications occurring with different moieties of the nucleic acid backbone are also within the scope of this invention. For example, the use of methyl phosphate or methyl phosphonate linkages to remove negative charges from the phosphodiester backbone can be used.

A specific binding complex is formed by base-pairing inteactions between the target and the capture ligand. The capture ligands of the present invention comprise a nucleic acid with a nucleotide sequence substantially complement to the nucleic acid sequence of the target molecule, or to a region, or portion, of then nucleic acid sequence of the target molecule wherein the target molecule hybridizes to the capture ligand. Possible base-pairing interactions useful in that method include duplexes that have canonical Watson-Crick base-pairing (reviewed in Cantor and Schimmel, *Biophysical Chemistry, Part I: The Conformation of Biological Macromolecules*, Ch. 3 and 6, Freeman, San Francisco, 1980) or noncanonical base-pairing schemes such as triple helix formation (Felsenfeld, Davies, and Rich, J. *Am. Chem. Soc.* ( 1957) 79:2023; for review see Doronina and Behr, Chem. Soc. Rev. (1997), p.63–71) and quadruplex formation (Sen and Gilbert, *Nature*(1990) 344:410–414; Sen and Gilbert, *Methods Enzymol.* (1992) 211:191–9).

Double stranded nucleic acids can be denatured into single-stranded components by heating or by chemical denaturants. The amount of the denaturant required to denature a given nucleic acid is dependent on the length of the dupex region, the base composition of the duplex, the nucleotide sequence of the duplex region, and on the presence of base mispairing within the duplex region. In general, GC rich sequences will have higher melting temperatures, and will require higher concentrations of chemical denaturant than AT rich sequences. Melting temperature is also strongly affected by nearest neighbor interactions within the duplex region. Thus, two duplexes with identical AT composition but different primary sequences can have significantly different melting properties. In addition, the presence of mispairs within a duplex region almost always lowers its melting temperature relative to the non-mispaired state.

In general, the same principles hold true for triplex and quadruplex nucleic acid structures, although the exact amount of denaturant required to denature these structures may differ significantly from duplex structures of similar base composition and length.

For the method of the present invention, it is not necessary to know the exactly how much the temperature or concentration of chemical denaturant needs to be lowered in order for the target to bind to the capture ligand and become immobilized. It is only necessary that the denaturant concentration wherein the target with the highest affinity for the capture ligand (i.e., the target which is most complementary to the capture ligand) does not bind to the capture ligand and the denaturant concentration wherein the target which has the lowest affinity for the capture ligand (i.e., the target which is least complementary to the capture ligand) binds to the capture ligand and becomes immobilized, both fall within the range of the denaturant gradient. Example 2 describes a method of determining the temperature at which a target nucleic acid will dissociate from a capture ligand within a gel using a temperature gradient gel. Similar experiments can be done using a chemical denaturing gradient gel to determine the amount of chemical denaturant needed to destabilize a target/capture ligand complex.

AN ELECTROPHORETIC MEDIUM WHICH CONTAINS AT LEAST ONE IMMOBILIZED CAPTURE LIGAND

Any medium suitable for electrophoresis, in which a capture ligand can be immobilized throughout, can be used for the methods of the present invention. In a preferred embodiment, the capture ligand is immobilized uniformly throughout the medium. In addition, more than one capture ligand can be immobolized throughout the medium. If more than one capture ligand is immobilized throughout the medium, the immobilized capture ligands are called a set or group of capture ligands.

In general, suitable media fall into two classes. The first includes media composed of gel-forming materials like crosslinked polyacrylamide and agarose. The second class includes media composed of solutions of linear non-cosslinked polymers such as polyacrylarnide, poly (hydroxyethylcellulose), and poly(ethyleneoxide). The latter category is commonly used for capillary electrophoresis applications.

Immobilization of ligands can be accomplished by direct attachment to the polymeric components of the medium. Such attachment can be mediated by formation of covalent bonds between the ligand and the polymer. Noncovalent binding between the ligand and polymer substituents can also be used. For instance, strong noncovalent binding provided by the widely-used biotinstreptavidin and digoxigenin-antidigoxigenin systems can be used to attach ligands to appropriately modified polymeric media. Covalent attachment is preferred.

Direct connection between the polymeric medium and the ligand is not strictly required. For instance, ligands can be attached to particulate supports, such as microspheres, and the particulate supports can be immobilized within the polymer medium by physical entrapment (Cantor, et al., U.S. Pat. No. 5 482,863, the teachings of which are incorporated herein by reference in their entirety). The particles may be macroscopic, microscopic, or colloidal in nature, (see Polyciences, Inc., 1995–1996 particle Catalog, Warrington, Pa.).

In a similar manner, ligands can be attached to highly branched soluble polymers. Due to their branched shape, such ligand-polymer complexes display extremely large effective hydrodynamic radii and, therefore, will not migrate in the electric field in many kinds of polymeric media of appropriately small pore size. Thus, they can be entrapped within the media in the same fashion as particulate supports.

Absolute immobilization of the ligand within the medium is not required for all embodiments of the invention. For many applications, it is sufficiant that the mobility of the target is changed upon formation of a binding complex with the ligand. This condition can be satisfied by coupling the ligand to a medium component that has extremely low electrophoretic mobility. However, for efficient separation the change in mobility should be as large as possible. Therefore, media utilizing true immobilization of the ligand within the medium will be preferred for use in this invention.

Commonly used gel media useful for the present invention include acrylamide and agarose gels. However, other materials may be used. Examples include modified acrylamides and acrylate esters (for examples see Polysciences, Inc., Polymer & Monomer catalog, 1996–1997, Warrington, Pa), starch (Smithies *Biochem. J.* (1959), 71:585; product number S5651, Sigrna Chemical Co., St. Louis, Mo.), dextrans (for examples see Polysciences, Inc., Polymer & Monomer Catalog, 1996–1997, Warrington, Pa.), and cellulose-based polymers (for examples see Quesada, *Current Opinions in Biotechnology*(1997), 8:82–93). Any of these polymers can be chemically modified to allow specific attachment of nucleic acid ligands for use in the present invention.

For some methods, it may be useful to use composite media, containing a mixture of two or more supporting materials. An example is the composite acrylamide-agarose gel. These gels typically contain from 2–5% acrylamide and 0.5%–1% agarose. In these gels the acrylamide provides the chief sieving function, but without the agarose, such low concentration acrylamide gels lack mechanical strength for convenient handling. The agarose provides mechanical support without significantly altering the sieving properties of the acrylamide. In such cases, the nucleic acid can be attached to the component that confers the sieving function of the gel, since that component makes most intimate contacts with the solution phase nucleic acid target.

For capillary electrophoresis (CE) applications it is convenient to use media containing soluble polymers. Examples of soluble polymers that have proven to be useful for CE analyses are linear polymers of polyacrylamide, poly(N,N-dimethylacrylamide), poly(hydroxyethylcellulose), poly(ethyleneoxide) and poly(vinylalcohol) as described in Quesada, *Current Opinion in Biotechnology*(1997), 8:82–93). Solutions of these polymers can also be used to practice the methods of the present invention.

Methods of coupling nucleic acid or modified nucleic acid ligands to create affinity electrophoresis media are well known to those skilled in he art. Many ligands can be coupled to agarose, dextrans, cellulose, and starch polymers using cyanogen bromide or cyanuric chloride activation. Polymers containing caboxyl groups can be coupled to ligands that have primary amine groups using carbodimide coupling. Polymers carrying primary amines can be coupled to amine containing ligands with glutaraldehyde or cyanuric chloride. Many polymers can be modified with thiol-reactive groups which can be coupled to thiol-containing ligands. Many other suitable methods are known in the literature. For examples, see Wong, "Chemistry of Protein Conjugation and Cross-linking", CRC Press, Boca Raton Fla., 1993.

Methods for covalently attaching ligands by copolymerization with the polymeric material of the electrophoretic medium have also been developed. In this approach, ligands are chemically modified with a copolymerizable group. When such modified ligands are copolymerized with suitable mixtures of polymerizable monomers, polymeric media containing high concentrations of immobilized ligand can be produced. Preferred methods for covalently attaching nucleic acids to polymerizable chemical groups are found in U.S. Patent application Ser. No. 08/812,105, U.S. Pat. No. 5,932,711 entitled "Nucleic Acid-Containing Polymerizable Complex" and U.S. Patent application Ser. No. 08/971,845, entitled "Electrophoretic Analysis of Molecules Using Immobilized Probes", the teachings of which are herein incorporated by reference, in their entirety. (See also, Rehman, et al., *Nucleic Acids Research*(1999), 27:649.) In this method, the gel contains a nucleic acid capture ligand immobilized at a uniform concentration throughout a crosslinked polyacrylamide gel.

Other approaches for attaching nucleic acid ligands to preformed polyacrylamide polymers, including gels or linear soluble polymers can be found in Ghosh and Fahy, U.S. Pat. No. 5,478,893, the teachings of which are incorporated herein by reference in their entirety, and in Timofeev et al., *Nucleic Acids Res*. (1996 ), 24:3142–3148.

SPATIAL GRADIENT OF A NUCLEIC ACID DENATURANT

In addition to having an immobilized capture ligand, the electrophoretic medium has a spatial gradient of a nucleic acid denaturant. Denaturants are conditions or chemicals which disrupt the binding of the target to the capture ligand. Examples of denaturants include temperature or chemical denaturants, such as urea or formamide. The denaturant gradient is orientated parallel to the direction of the electric field gradient such that the target will migrate from a region of high denaturing activity to a region of low denaturing activity when the electric field is applied. In the region of the medium where the denaturing activity is high the ligand has relatively low binding affinity or no binding affinity for the target. In the region of the medium where the denaturing activity is low the ligand has a relatively high affinity for the target. Preferably the denaturing gradient will have a region where the capture ligand will have no binding affinity for the target and will gradually progress to a region wherein the binding affinity of the capture ligand for the target high enough to substantially immobilize the target.

A temperature gradient is a preferred denaturing gradient. A temperature gradient can be imposed on the medium by a temperature control apparatus. A temperature control apparatus maintains the area of the medium where the sample will be introduced (e.g., the area near the sample wells in a slab gel or the end of a capillary where the sample is introduced in capillary electrophoresis) at high temperature and, simultaneously, maintains the area at the opposing end of the medium (e.g., the lower end of a slab gel or the end of the capillary where the sample is detected in capillary electrophoresis) at lower temperature. An example of a temperature control apparatus can be seen in FIG. 1. Preferably, the temperature where the sample is introduced into the medium is too high to allow the target to bind to the capture ligands and the temperature at the opposite end of the electrophoretic medium is below the temperature at which a target binds to the capture ligand (e.g., below the Td for a particular target nucleic acid/capture ligand binding complex).

As the sample progresses through the medium to an area of the medium where the denaturing activity is moderate, the binding between capture ligand and target molecule becomes transient and rapidly reversible on the time scale of the electrophoretic analysis. Under these conditions, target molecules undergo many cycles of binding, dissociation, and rebinding to the capture ligand as the target progresses through the medium. This reversible binding has the effect of reducing the electrophoretic mobility of the target measured relative to its mobility in the absence of capture ligand. As the target nucleic acid progresses still further to an area of the medium where the denaturant activity is low, binding to the capture ligand is strong, and, eventually, the target forms a stable complex with the capture ligand and becomes immobilized in the medium. Nucleic acids targets containing a sequence complementary to the capture ligand will bind more strongly to the capture ligand than nucleic acids targets which have one or more mismatches with the capture ligand. This causes the nucleic acid targets with completely complementary sequences to stop in the gel at a different position than nucleic acid targets that have one or more mismatches. In this way, structurally related targets which have similar electrophoretic mobilities in the absence of capture ligand, can be distinguished on the basis of their affinity for a specific capture ligand.

Processes and means for establishing a temperature gradient in the electrophoretic media are well known to those skilled in the art. For example, Thatcher and Hodson, *Biochem. J*. (1981) 197:105–109, demonstrated a method of imposing a temperature gradient on a gel in order to study the melting behavior of nucleic acids. In addition, Rosenbaum and Riesner, *Biophys. Chem.* (1987), 26:235–246, described the use of temperature gradient gels in which the temperature gradient is aligned in parallel with the direction of electrophoresis so that the samples migrate from cooler to warmer regions of the gel. Temperature-controlled equipment for performing vertical or horizontal fonmat electrophoresis are commercially available (Bio-Rad Life Science Research Products Catalog (1997), pp. 127–133, 175–182; Pharmacia Biotech BioDirectory (1997), pp. 345, 309, 334). In some instruments, temperature control is achieved by circulation of water (or suitable liquid) through a block in contacted with the electrophoretic medium (see, for example FIG. 1) . The block is made of a thermally conductive material, such as aluminum. In these instruments, a temperature gradient can be achieved by having two regulated reservoirs set at the desired temperatures. The reservoir which is at a higher temperature is circulated through a channel, or port, in the portion of the block in contact with the area of the electrophoretic medium where the sample is introduced. The reservoir which is at a lower temperature is circulated through a channel, or port, in the block which is in contact with the opposite end of the medium (see FIG. 1).

In one especially preferred embodiment of the invention, the capture ligand is a single strand nucleic acid and the target is a sample nucleic acid that has at least one region complementary to the nucleic acid sequence of the capture ligand. In this case, the binding between target and ligand can be effectively modulated by changing the gel temperature. For example, at temperatures above the Td of the target/capture ligand complex, binding affinity will be low. Similarly, at temperatures below the Td, binding affinity will be substantially higher.

Changing the medium temperature is one preferred mean for modulating target/ligand binding affinity, since temperature can be varied with little or no manipulation of the electrophoresis medium, and since a great deal of instrumentation for temperature control is commercially available. However, other medium properties may be used as well. A non-limiting list of possible properties which are known to affect noncovalent chemical associations include changes in medium pH, changes in the ionic strength of the medium, and other changes in chemical composition of medium such as addition of formamide or urea.

A denaturant gradient can also be established with chemimal denaturants such as urea or formamide (see Creighton, *J Mol. Biol.* (1979) 129:253–264 and Fischer, et al., *Cell* (1979) 16:191–200, the teachings of which are incorporated wherein by reference in their entirety). The amount of denaturant required in the most dematuring part of the gradient will depend on the type of target molecule, the strength of affinity binding interaction between the target and the capture ligand, field strength, ionic strength, and temperature of electrophoresis. In general, a chemical denaturant can be present in the medium in a very broad concentration range. For example, formiamide can be used in concentrations up to 95% (volume/volume), and urea can be used at concentrations up to 8M. Hybridization experiments can also be used to provide a rationale for predicting the stability of the target/capture ligand binding complex in a particular concentration of chemical denaturant.

A KIT FOR DETECTING A MUTATION IN A NUCLEIC ACID TARGET

One aspect of the present invention is a kit for analyzing a nucleic acid sequence of a target nucleic acid in a test sample for the presence of at least one degenerate site, or mutation. In one embodiment, the kit includes an electrophoretic medium that has at least one immobilized capture ligand that is complementary to at least one region, or portion, of the nucleic acid sequence of the target that encompasses the degenerate site, or mutation. The capture ligand is designed to type the degenerate site, or mutation. A capture ligand is designed to type a degenerate site, or mutation if it is complementary to a region of the nucleic acid sequence of the target surrounding the site and is complementary to one of the degenerate options at the degenerate site.

In another embodiment, in addition to including an electrophoretic medium that has at least one immobilized capture ligand, the kit also includes a spatial gradient of a nucleic acid denaturant within the electrophoretic medium, such a chemical gradient within the medium or a means for imposing a temperature gradient within the medium.

In a preferred embodiment, in addition to including an electrophoretic medium that has at least one immobilized capture ligand, the kit can include enzymatic amplification reagents, for example PCR reagents, for amplification of the target. Amplification reagents preferably include labeled deoxynucleotide triphosphates (hereinafter "dNTP") so that the target is label (e.g., radiolabeled or fluorescent labeled) during the amplification step. This type of kit can also include a chemical denaturing gradient in the electrophoretic medium or a means for imposing a temperature gradient within the medium.

The electrophoretic medium included in each type of kit described above can have a set of immobilized capture ligands, each of which is complementary to a different region of the target nucleic acid sequence which contains a degenerate site, or mutation.

STANDARDS

In order to determine the degree of complementarity been the target nucleic acid sequence and the capture ligand and, thus analyze the nucleic acid sequence of the target, one or more standards can be electrophoresed simultaneously with the target nucleic acid or separately from the target nucleic acid but under the same electrophoretic conditions. A standard is a nucleic acid in which all or a portion of its sequence is a known or predetermined sequence that is the same as the portion of the target nucleic acid sequence which is complementary to the capture ligand. One or more standards can be used to analyze a nucleic acid sequenced, in a preferred embodiment, the sequences of the standard will be the same as one or more expected target nucleic acid.

Other types of nucleic acid standard can also be used depending on the target nucleic acid to be analyzed. For example, if it is desirable to determine if a target nucleic acid has one mismatch to the capture ligand, a nucleic acid standard with that has a sequence containing one mismatch to the capture ligand can be used.

A kit for analyzing a nucleic acid sequence of a target for the presence of a mutation, or a degenerate site, can optionally contain a set of standards which vary in complementarity to a set of capture ligands immobilized in the electrophoretic medium contained in the kit. For example, the kit which has an electrophoretic medium which has a set of two capture ligands for analyzing two biallelic sites (for example, the two biallelic sites in FIG. 2) could have four standards which correspond to the four nucleic acid sequences expected for the four target nucleic acids.

Alternatively, a target nucleic acid sequence can be analyzed without using a standard if the experimental conditions for analysis are sufficiently discriminating and reproducible. For instance, when typing the sequence of one billelic site, all targets will fall into only two classes. In the first class are targets that bind under relatively high denaturing conditions (e.g., high temperature or high conccentration of chemical denaturant). In the second class are targets that bind under low or denaturing conditions than the targets in the first class (e.g., lower temperature or low concentration of chemical denaturant). FIG. 2B shows an idealized picture of a gel after an experiment has been run to type one biallelic site. In such cases, standards are not always required, especially when many samples are run on the same apparatus under the same conditions.

DETECTION SCHEMES

Detection of the specific binding reaction, e.g., detection of the immobilized target molecule bound to the capture ligand, can be accomplished in a number of different ways. For example, the target nucleic acid in a test sample can be detectably labeled prior to the binding reaction. Suitable labels for direct target labeling can be intensely absorbing (e.g., brightly colored), radioactive, fluorescent, phosphorescent, chemiluminescent or catalytic. Direct target labeling of nucleic acid samples using modified nucleotides can be accomplished by a number of enzymatic methods well known to those practiced in the art (reviewed in Sambrook, et al. "Molecular Cloning: A Laboratory Manual", 2nd edition, Cold Spring Harbor Press, Cold Spring Harbor, N.Y 1989). In a preferred embodiment of this invention, the target is produced by a PCR reaction which utilizes labeled deoxynucleotide triphosphates (hereinafter "dNTP"), tereby producing a detectably labeled nucleic acid target. dNTPs labeled with a radioactive label, for example $^{32}P$, or a fluorescent label are particularly useful for this purpose.

Alternatively, the target molecule can be labeled indirectly using a ligand which can be recognized by a second specific binding entity which is either labeled itself or can produce a detectable signal. An example of such an indirect system is labeling using biotinylated nucleotides. In this system, the sample is labeled enzymatically using standard nucleic acid labeling techniques and biotinylated nucleotides. The resulting biotin-modified nucleic acids can be detected by the biotin-specific binding of streptavidin or avidin proteins molecules. The streptavidin or avidin molecules can be conjugated to fluorescent labels, such as fluorescein or reporter enzymes, such as alkaline phosphatase or horseradish peroxidase, which can be used to produce chemiluminescent or colorimetric signals with appropriate substrates (for review see Keller and Manak, "DNA Probes", 2nd ed., Macmillan Publishers, London, 1993; Pershing, et al., eds "Diagnostic Molecular Microbiology: Principles and Applications", American Society for Microbiology, Washington, D.C., 1993). Another useful detection system is the digoxigenin system which uses an anti-digoxigenin antibody, conjugated to alkaline phosphatase, which recognizes digoxigenin-dUTP incorporated into nucleic acids. (Ausubel, F. M., Current Protocols in Molecular Biology(1995), ed., vol.1, §§ 3.18.1 to 3.19.6).

Detectably labeled hybridization probes can also be used as indirect target labels. For example, target nucleic acids can be indirectly labeled prior to electrophoresis by hybridization with a detectably labeled probe, hereafter termed a "sandwich" probe. The sandwich probe is designed to hybridize with a region of the target which does not overlap the region recognized by the capture ligand. The sandwich probe is designed to remain associated with the target during electrophoresis, and cannot bind directly to the capture ligand.

Sandwich probes can also be used to label target molecules after electrophoretic capture. In this labeling strategy, the unlabeled target is electrophoresed and hybridized to the capture ligands first. Then, the sandwich probe is electrophoresed through the capture layer. In effect, the captured target now acts as a new "capture" ligand for the sandwich probe. The captured target sandwich probe complex can now be detected through the sandwich probe label.

Blotting techniques can also be adapted for detection of target bound capture ligands. For example, a detection surface is juxtaposed to the separation medium having bound sample components, and the sample components then migrate to the detection surface, optionally assisted by, for example, chemical means such as solvent or reagent changes, where the transferred sample components are detected by known means such as optical detection of intercalating dyes, or by detection of radioactivity from hybridized radioactive species, or other known means.

A variety of optical techniques can be used to detect the presence of sample components bound to the capture ligands. For example, the position and intensity of each signal may be measured by mechanically or optically scanning a single detector over the electrophoretic medium after a target has been electrophoresed through the medium.

TYPING OF AN INDIVIDUAL FOR SICKLE CELL ANEMIA

Many genetic diseases are a consequence of a specific mutation at a particular site in a gene. For example, sickle cell anemia is causes by a point mutation in the gene which codes for hemoglobin. In this case, the substitution of a thymine for an adenosine results in a hemoglobin molecule which has a valine amnino acid in place of glutamic acid (i.e., there is a biallelic site in the hemoglobin gene). The mutated hemoglobin is less soluble when it is deoxygenated which result in symptoms such as anemia, shortness of breath and organ damage. A portion of the population which is heterozygous for the hemoglobin gene is generally asymptomatic but can experience symptoms at high altitude.

The method of the present invention can be used to determine whether an individual has the sickle cell trait. A capture ligand which spans the biallelic site in the hemoglobin gene is immobilized at a uniform concentration through out an electrophoretic medium such as a polyacrylamide gel. The immobilized capture ligand can be completely complementary to the a portion of the genetic sequence of normal hemoglobin (i.e., hemoglobin A), or it can be completely complementary to the genetic sequence of sickle cell hemoglobin (i.e., hemoglobin S).

To determine whether an individual has sickle cell anemia, a sample of genetic material can be obtained from the individual and the hemoglobin gene can be excised using restriction enzymes. Standard electrophoresis techniques can be used to obtain a test sample that has nucleic acids of a particular length and which encompasses the hemoglobin gene. This sample can be electrophoresed through a gel that contains a capture probe for a portion of the hemoglobin gene that contain the biallelic site. The target nucleic acids can then be detected using a technique such as southern blotting.

An alternative procedure for obtaining a target which contains the hemoglobin gene from an individual is to amplify the hemoglobin fragment of the gene containing the site of the sickle cell mutation, using an enzymatic amplification technique, such as PCR. Fluorescent labeled or radioactively labeled dNTPs can be used in the enzymatic amplification step to produce a labeled target which can be detected directly in the gel.

A kit for determining whether an individual is homozygous for hemoglobin A, homozygous for hemoglobin S or heterozygous would include an electrophoretic medium, such as an acrylamide gel, with an immobilized capture ligand that is complementary to the region of the nucleic acid sequence of hemoglobin which contains the mutation. The kit would also have a means for creating a denaturant gradient, such as a temperature control apparatus or a chemical gradient in the electrophoretic medium. If a capture ligand is selected that is completely complementary to the sequence of hemoglobin S, then a test sample which contains a target nucleic acid sequence for hemoglobin S will stop higher up on the gel in an area where the denaturing activity is higher than a sample which contains hemoglobin A. The mobility of the target nucleic acid in a test sample can be measured against, or compared to, a standard nucleic acid sequence included in the kit which is the same fragment as the test sample but which is known to contains the nucleic acid sequence for hemoglobin A. Optionally, the kit could include two standards, one which contains the nucleic acid sequence for hemoglobin A and one which contains the nucleic acid sequence for hemoglobin S. Thus, it can be determined whether an individual is homozygous for hemoglobin A, homozygous for hemoglobin S or heterozygous by comparing the mobility of the target nucleic acid in the test sample to the mobility of the standards contained within the kit.

Figure 3:
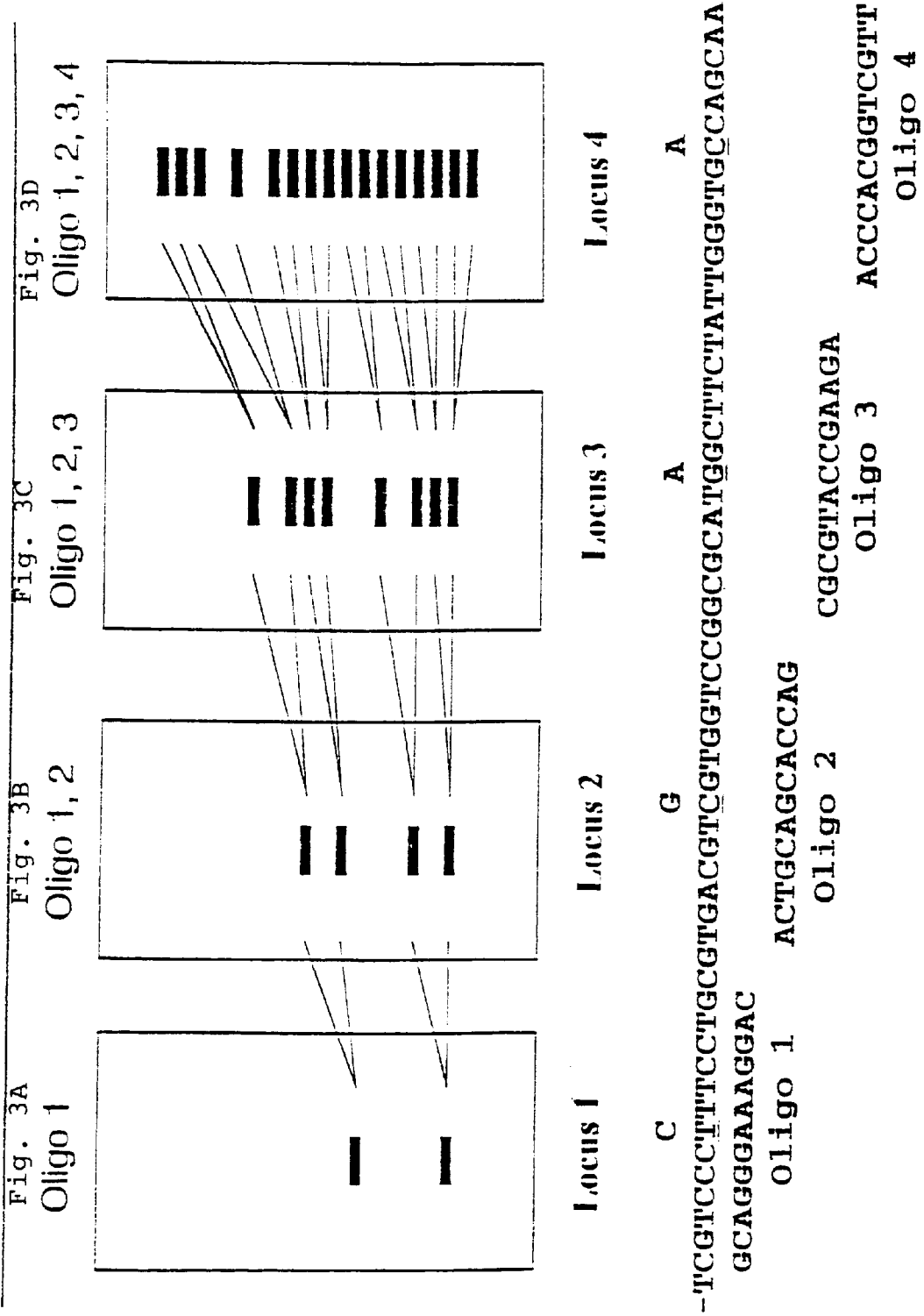
FIGS. 3A–3D are a graphic illustration of the principle of denaturant gradient affinityelectrophoresis of a target nucleic acid (SEQ ID NO:2) that has four biallelic markers labeled loci 1 –4.

Genetic disorders caused by mutations in more than one degenerate site can also be detected by the method of the invention (see FIG. 3). In such cases, capture ligands, complementary to a portion of the nucleic acid sequence containing each degenerate site could be immobilized in an electrophoretic medium. A test sample could be electrophoresed through the medium and its mobility compared to standards containing a known set of alleles. By matching the mobility of the target nucleic acid in the test sample to the mobility of a standard, the set of alleles which the target has can be determined.

The following specific examples are provided to illustrate the methods and apparatus contemplated for use in the instant invention. They are not intended to limit the invention in any way.

EXAMPLES

Example 1
Denaturant Gradient Affinity Electrophoresis Typing of a Nucleic Acid Target That Has Two Biallelic Sites FIG. 4 shows an experiment using model targets based on the sequences shown in FIG. 2. Four fluorescein tagged oligonucleotides representing the four possible haplotypes of the sequence shown at the bottom of FIG. 4 were electrophoresed through a 10% polyacrylamide gel (29:1, monomer:bisacrylamide) containing 1XTBE (89 mM Trisborate, pH 8.3, 2 mM EDTA). The gel was cast with 1 µM 5'-acrylamide olignucleotide capture ligand (oligonucleotide synthesized with 5'-Acrydite modification, Operon Technologies, Almeda, Calif.). The sequence of the capture ligand is shown at the bottom of FIG. 4. In this experiment, the two sequences corresponding to Oligo 1 and Oligo 2 in FIG. 2 were fused together via a four base poly T linker sequence (the linker is not complementary to the target) to create a single capture ligand with dual binding specificity. Electrophoresis was carried out in a device similar to that shown in FIG. 1, and a linear temperature gradient was maintained using 50° C at the top and 20° C at the bottom. Following electrophoresis, the pattern of fluorescent oligonucleotides was visualized using a Molecular Dynamics Fluorimager. As seen, all four haplotypes were clearly resolved and the final position of each model target correlates well with the predicted affinity of each target for the capture ligand. Thus, the completely complementary G/C target binds highest up in gel the C/T target with two mispairs binds at the lowest position, while the G/T and C/C targets bind at intermediate positions as expected since each have one mispair with the target. The G/T target binds slightly tighter than the C/C target since the G/T target contains the least destabilizing mispair (capture ligand strand G paired with G/T target strand T).

Example 2
The Use of Temperature Gradient Gel Electrophoresis for Evaluating a Target Nucleic Acid/Capture Ligand Complex Td During Electrophoresis The following example illustrates the general use of temperature gradient gels to estimate Td (the temperature at which 50% of the hybridization omplex has dissociated during the time of electrophoresis) of a particular immobilized duplex (hybridization complex consisting of two nucleic acid sequences, for example a target nucleic acid and a capture ligand) under electrophoresis conditions. Deoxyribonucleic acid nucleic acid sequences were prepared by the phosphoramidite synthesis method and purified using ion exchange chromatograph, size exclusion chromatograph or reverse phase High Performance Liquid Chromatography (HPLC) (Operon, Integrated DNA Technologies, Almeda, Calif.). Reverse phase HPLC is a preferred purification method. The sequence of the immobilized DNA polynucleotide sequence used was 5'-acrylamide-TTGGTTGGTTTATCGTTTTTG-3'(SEQ ID NO: 10). The 5'acrylamide moiety was added during automated synthesis using an acrylamide phospho amidite (Acrydite™, Mosaic Technologies, Boston, Mass.). The labeled complementary polynucleotide sequence was 5'-CY3-CAAAAACGATAAACCAACCA-3'(SEQ ID NO: 11).

Polyacrylamide gels (22 cm×16.5 cm×0.75 cm) were prepared and poured in 3 sections, all containing 1×TBE. The acrylamide (BioRad) concentration was 12% (29:1 monomer to bis wt ratio). The top and bottom sections contained no nucleic acid sequence, while the center section (1 mL total volume) contained the immobilized nucleic acid, or capture ligand, sequence at 3 µM. Polymerization was catalyzed by the addition of 1/100 th volume of 10% ammonium persulfate (APS) and 1/1000th volume of TEMED. To ensure smooth layers, the bottom and center layers were overlaid with 100% ethanol during polymerization. Gels were assembled in a single upright electrophoresis device (CBS Scientific).

A temperature gradient from 35° C. to 65° C. was established across the gel by clamping to the glass plate an aluminum block through which low and high temperature water circulated on opposite ends. The temperature gradient thus obtained was measured by reading the temperature in each well of the gel with a thermister and was found to be linear throughout the center of the gel.

The target nucleic acid sequence was diluted in gel loading buffer (8% sucrose, 1×TBE, bromophenol blue and xylene cyanol) and an equal amount (approximately 5 pmol) was loaded in each lane. Electrophoresis was performed at 150 V for approximately 1 h.

Figure 5:
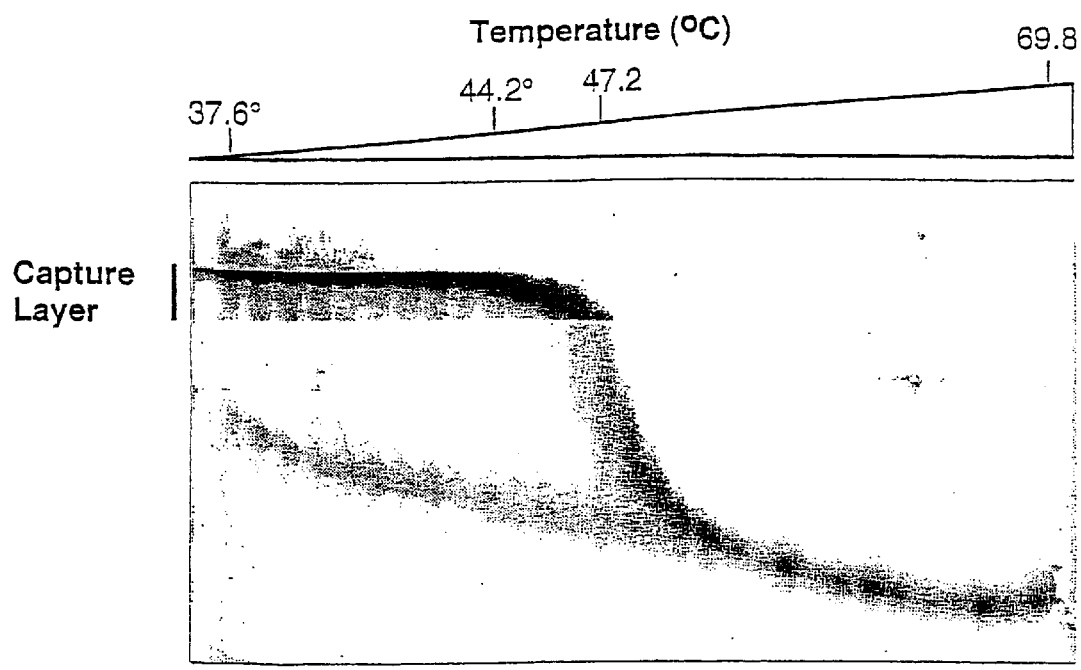
FIG. 5 is a image of a gel showing the results of an experiment to determine the Td of a target nucleic acid/ capture ligand complex.

Images were obtained by scanning gels on a Molecular Dynamics fluorimager. Fluorimetric analysis of the image allows determination of the position, and therefore, the temperature at which 50% of the labeled nucleic sequence is lost from the capture layer (see FIG. 5). This temperature represents the Td of a particular nucleic acid sequence/capture ligand complex.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for analyzing the nucleic acid sequence of at least one target nucleic acid comprising the steps of:
   a) contacting the target nucleic acid with an electrophoretic medium comprising:
      i) at least one nucleic acid capture ligand immobilized in the medium, and
      ii) a spatial gradient of a nucleic acid denaturant;
   b) applying an electric field oriented in a direction parallel to the denaturant gradient under conditions wherein the target sample migrates from a region of high denaturant activity to a region of low denaturant activity and, wherein the target nucleic acid binds to the immobilized capture ligand at a position within the medium relative to the binding affinity between the target and capture ligand; and c) determining one of the following properties:
  i) the position of the target within the medium, or
  ii) the electrophoretic mobility of the target in the medium, wherein the properties of the target determined in part c) are dependent on the nucleotide sequence or structure of the target nucleic acid.

2. The method of claim 1, wherein a property determined part c) is compared to the same property of a standard having a predetermined nucleic acid sequence.

3. The method of claim 1, wherein the capture ligand is a modified nucleic acid.

4. The method of claim 1, wherein the capture ligand is a nucleic acid analog.

5. The method of claim 4, wherein the nucleic acid analog is a peptide nucleic acid.

6. The method of claim 2, wherein the predetermined nucleic acid sequence of the standard is the same as the sequence of at least one target.

7. The method of claim 1, wherein the electrophoresis medium is polyacrylamide a modified polyacrylamide. or a modified polvacrvlate ester.

8. The method of claim 1, wherein the electrophoresis medium is agarose.

9. The method of claim 1, wherein the electrophoresis medium is a soluble linear polymer.

10. The method of claim 1, wherein more than one nucleic acid capture ligand is immobilized throughout the electrophoresis medium.

11. The method of claim 1, wherein a single nucleic acid capture ligand, comprising more than one capture subsequence complementary to more that one region of the target, is immobilized throughout the electrophoresis medium.

12. The method of claim 1, wherein the denaturant is temperature.

13. The method of claim 1, wherein the denaturant is a chemical.

14. The method of claim 13, wherein the denaturant is urea or formamide.

15. The method of claim 1, further comprising the step of amplifying the target using an enzymatic amplification technique.

16. The method of claim 15, wherein the enzymatic amplification technique is PCR.

17. The method of claim 16, wherein at least one labeled deoxynucleotide triphosphate is used in the amplification technique.

18. The method of claim 1, wherein the target is detectably labeled.

19. The method of claim 18, wherein the target is directly labeled with a noncovalently bound detectable moiety.

20. The method of claim 18, wherein the target is indirectly labeled with a noncovalently bound detectable moiety.

21. A method of analyzing at least one target nucleic acid from other components in a test sample comprising the steps of:
  a) contacting the test sample with an electrophoretic medium comprising
    ii) at least one nucleic acid capture ligand immobilized in the medium, and
    ii) a spatial gradient of a nucleic acid denaturant; and
  b) applying an electric field oriented in a direction parallel to the denaturant gradient under conditions wherein the target sample migrates from a region of high denaturant activity to a region of low denaturant activity and, wherein the target nucleic acid binds to the immobilized capture ligand at a position within the medium that is relative to the binding affinity between the target and the capture ligand;
  c) turning off the electric field after the target nucleic acids bind to the immobilized capture ligand;
  d) increasing the denaturant activity to a point wherein the target nucleic acids does not bind to the capture ligand;
  e) reapplying the electric field;
  f) determining a time at which a target nucleic acid passes a position in the medium which is detected by a detector, said detector detecting a position in the electrophoretic medium which is a greater distance, measured in the direction in which the target has migrated in step b), from the position wherein the electrophoretic medium was contacted with the test sample than all of the target nucleic acid have migrated, thereby analyzing the target nucleic acid.

22. The method of claim 21, further comprising the step of comparing the time for a target to reach the position detected by the detector to a time at which a standard nucleic acid reaches the position detected by the detector.

23. The method of claim 22, wherein the predetermined nucleic acid sequence of the standard is the same as at least one target.

24. The method of claim 21, wherein the electrophoretic medium is contained in a capillary electrophoresis apparatus.

25. The method of claim 21, wherein the electrophoretic medium is a slab gel.

* * * * *